(12) United States Patent
Kauschke et al.

(10) Patent No.: US 10,682,265 B2
(45) Date of Patent: Jun. 16, 2020

(54) NONWOVEN WITH IMPROVED ABRASION RESISTANCE AND METHOD OF MAKING THE SAME

(71) Applicant: First Quality Nonwovens, Inc., Great Neck, NY (US)

(72) Inventors: Michael Kauschke, Prien (DE); John C. Parsons, Dallas, PA (US); Michele Miller, Weatherly, PA (US)

(73) Assignee: PFNONWOVENS LLC, Hazelton, PA (US)

( * ) Notice: Subject to any disclaimer, the term of this patent is extended or adjusted under 35 U.S.C. 154(b) by 0 days.

(21) Appl. No.: 15/351,133

(22) Filed: Nov. 14, 2016

(65) Prior Publication Data

US 2017/0137980 A1 May 18, 2017

Related U.S. Application Data

(60) Provisional application No. 62/254,496, filed on Nov. 12, 2015.

(51) Int. Cl.
| | |
|---|---|
| *A61F 13/511* | (2006.01) |
| *D04H 3/14* | (2012.01) |
| *B32B 3/26* | (2006.01) |
| *B32B 3/30* | (2006.01) |
| *B32B 7/05* | (2019.01) |

(Continued)

(52) U.S. Cl.
CPC ........ *A61F 13/51104* (2013.01); *B32B 3/263* (2013.01); *B32B 3/266* (2013.01); *B32B 3/30* (2013.01); *B32B 7/05* (2019.01); *D04H 1/49* (2013.01); *D04H 1/495* (2013.01); *D04H 3/14* (2013.01)

(58) Field of Classification Search
CPC ....... Y10T 428/24802; Y10T 428/2481; Y10T 428/24826; D10B 2501/00; D10B 2403/0331; D06C 15/02; D06C 15/04; D06C 15/06; A61F 13/51104
See application file for complete search history.

(56) References Cited

U.S. PATENT DOCUMENTS

| | | |
|---|---|---|
| 364,724 A | 6/1887 | Morgan |
| D18,428 S | 7/1888 | Koskul |
| D68,506 S | 10/1925 | Bluhm |

(Continued)

FOREIGN PATENT DOCUMENTS

| | | |
|---|---|---|
| EP | 1342825 A1 | 9/2003 |
| EP | 2479331 A1 | 7/2012 |

(Continued)

OTHER PUBLICATIONS

International Search Report of the International Searching Authority relating to International Application No. PCT/US2016/061891, dated Feb. 1, 2017.

(Continued)

*Primary Examiner* — Z. Jim Yang
(74) *Attorney, Agent, or Firm* — Amster, Rothstein & Ebenstein LLP (57) ABSTRACT

A nonwoven web made up of continuous fibers that include a polymer component, the web being bonded by a bond pattern including spaced apart closed figures arranged in a repeating pattern, the web having an abrasion rating of 3 or higher and an average HOM of less than 6 grams.

46 Claims, 9 Drawing Sheets

(51) Int. Cl.
*D04H 1/49* (2012.01)
*D04H 1/495* (2012.01)

(56) References Cited

U.S. PATENT DOCUMENTS

| | | |
|---|---|---|
| D87,085 S | 5/1932 | Schindler |
| D88,397 S | 11/1932 | Christen |
| D90,401 S | 8/1933 | Cusson |
| D99,618 S | 5/1936 | Daniels |
| D99,638 S | 5/1936 | Daniels |
| D99,856 S | 6/1936 | Daniels |
| D100,933 S | 8/1936 | Burgess |
| D101,820 S | 11/1936 | Perkins |
| D110,500 S | 7/1938 | Schubart |
| D113,619 S | 3/1939 | Berlinger |
| D117,065 S | 10/1939 | Huber |
| D117,984 S | 12/1939 | Tillman |
| D124,237 S | 12/1940 | Oltarsh |
| D124,700 S | 1/1941 | Schwartz |
| D125,362 S | 2/1941 | Zavell |
| D125,867 S | 3/1941 | Roth |
| D126,642 S | 4/1941 | Salzenstein |
| D129,870 S | 10/1941 | Maisch |
| D133,264 S | 8/1942 | Perkins |
| D166,917 S | 6/1952 | Koeber |
| 2,721,810 A | 10/1955 | Schram |
| 2,799,870 A | 7/1957 | Sullivan |
| D182,817 S | 5/1958 | Howell et al. |
| 3,065,520 A | 11/1962 | Schmidt |
| D196,426 S | 10/1963 | Lesser |
| 3,655,501 A | 4/1972 | Tesch |
| 3,764,450 A | 10/1973 | Tesch |
| D232,784 S | 9/1974 | Hirschl |
| 3,857,144 A | 12/1974 | Bustin |
| 3,925,127 A | 12/1975 | Yoshioka |
| 3,953,638 A | 4/1976 | Kemp |
| 3,959,546 A | 5/1976 | Hill |
| 4,165,403 A | 8/1979 | Alban |
| D253,424 S | 11/1979 | Roeder |
| D253,426 S | 11/1979 | Roeder |
| D253,550 S | 11/1979 | Roeder |
| D259,219 S | 5/1981 | Bates et al. |
| 4,333,979 A | 6/1982 | Sciaraffa et al. |
| 4,493,868 A | 1/1985 | Meitner |
| 4,567,080 A | 1/1986 | Korsgaard |
| 4,587,175 A | 5/1986 | Akao |
| D287,195 S | 12/1986 | Billgren |
| 4,654,244 A | 3/1987 | Eckert et al. |
| 4,671,983 A | 6/1987 | Burt |
| D291,845 S | 9/1987 | Lamborghini |
| 4,698,257 A | 10/1987 | Goll |
| 4,741,793 A | 5/1988 | Jones |
| 4,908,251 A | 3/1990 | Iimura et al. |
| 4,963,412 A | 10/1990 | Kokeguchi |
| D341,490 S | 11/1993 | Curran et al. |
| D349,159 S | 7/1994 | Huffman |
| D363,610 S | 10/1995 | Saffran et al. |
| 5,455,109 A | 10/1995 | Atkinson et al. |
| 5,458,938 A | 10/1995 | Nygard et al. |
| 5,470,434 A | 11/1995 | Terasawa et al. |
| D367,764 S | 3/1996 | Makoui et al. |
| D367,766 S | 3/1996 | Makoui et al. |
| D371,866 S | 7/1996 | Gerhartl |
| D371,910 S | 7/1996 | Schulz |
| D382,713 S | 8/1997 | Giesler, Sr. |
| D384,820 S | 10/1997 | Choi |
| 5,673,489 A | 10/1997 | Robell |
| 5,833,804 A | 11/1998 | Ruppel et al. |
| 5,834,099 A | 11/1998 | Steinhardt et al. |
| 5,840,633 A | 11/1998 | Kurihara et al. |
| 5,858,505 A | 1/1999 | Moen et al. |
| 5,874,157 A | 2/1999 | Robinson et al. |
| D410,051 S | 5/1999 | Sassak |
| 5,964,742 A * | 10/1999 | McCormack .......... D04H 1/54 428/198 |
| D419,780 S | 2/2000 | Funk et al. |
| D420,808 S | 2/2000 | Dwiggins et al. |
| 6,049,987 A | 4/2000 | Robell |
| D425,113 S | 5/2000 | Kleman et al. |
| D428,267 S | 7/2000 | Romano, III et al. |
| 6,093,665 A | 7/2000 | Sayovitz et al. |
| D429,074 S | 8/2000 | Hurst et al. |
| D429,939 S | 8/2000 | Denney |
| 6,109,326 A | 8/2000 | Leakey et al. |
| D430,407 S | 9/2000 | Ingalls |
| D438,962 S | 3/2001 | Velazquez et al. |
| D440,772 S | 4/2001 | Visel |
| 6,261,666 B1 | 7/2001 | Enderby et al. |
| 6,277,466 B1 | 8/2001 | McNeil et al. |
| D448,574 S | 10/2001 | Graff et al. |
| D448,575 S | 10/2001 | Graff et al. |
| D449,452 S | 10/2001 | Graff et al. |
| D449,453 S | 10/2001 | Duritsch et al. |
| D451,289 S | 12/2001 | Visel |
| D454,433 S | 3/2002 | Peter |
| 6,383,958 B1 | 5/2002 | Swanson et al. |
| D463,137 S | 9/2002 | Monroe et al. |
| D478,661 S | 8/2003 | Levy et al. |
| 6,610,390 B1 * | 8/2003 | Kauschke ............. B32B 5/26 428/198 |
| 6,687,962 B2 | 2/2004 | Clarner et al. |
| 6,749,924 B2 | 6/2004 | Monson et al. |
| 6,797,377 B1 | 9/2004 | DeLucia et al. |
| 6,858,285 B1 | 2/2005 | Hamilton et al. |
| D502,583 S | 3/2005 | Hardy et al. |
| D504,779 S | 5/2005 | Leisch et al. |
| D506,071 S | 6/2005 | Delaney |
| 6,921,502 B1 | 7/2005 | Nord et al. |
| 6,959,505 B2 | 11/2005 | Poe |
| 7,037,580 B2 | 5/2006 | Razavi et al. |
| 7,045,197 B2 | 5/2006 | Harris |
| 7,097,892 B2 | 8/2006 | Sano |
| 7,246,824 B2 | 7/2007 | Hudson |
| D555,911 S | 11/2007 | Simoni et al. |
| 7,303,650 B2 | 12/2007 | Hermans et al. |
| D562,568 S | 2/2008 | Johnston et al. |
| D564,721 S | 3/2008 | Vinson et al. |
| D581,170 S | 11/2008 | Delaney |
| D584,515 S | 1/2009 | Storz |
| D589,611 S | 3/2009 | Parker |
| D590,158 S | 4/2009 | Rushworth |
| D613,949 S * | 4/2010 | Mercer .................. B32B 5/26 D5/37 |
| D620,715 S | 8/2010 | Spitzer |
| D625,111 S | 10/2010 | Carrier et al. |
| 7,805,818 B2 | 10/2010 | Horn et al. |
| D629,210 S | 12/2010 | Hong |
| D630,441 S | 1/2011 | Wiwi et al. |
| D633,673 S | 3/2011 | McKnight |
| 7,895,718 B2 | 3/2011 | Horn et al. |
| 7,914,723 B2 | 3/2011 | Kim et al. |
| D643,427 S | 8/2011 | McGoldrick et al. |
| D653,844 S | 2/2012 | Smith |
| D668,058 S | 10/2012 | Morrow, III |
| D670,917 S | 11/2012 | Blackford |
| D671,754 S * | 12/2012 | Romano, III .......... D04H 1/544 D5/59 |
| D681,964 S * | 5/2013 | Romano, III .......... A61F 13/00 D5/59 |
| D684,162 S | 6/2013 | Aoshima |
| D685,998 S | 7/2013 | Robbins, III et al. |
| 8,512,515 B2 | 8/2013 | Dyer et al. |
| D701,049 S | 3/2014 | Riddle |
| D702,047 S | 4/2014 | Rhodes, III et al. |
| D702,447 S | 4/2014 | Boyle |
| D704,479 S | 5/2014 | Gatto |
| D706,038 S | 6/2014 | Choi |
| D711,113 S | 8/2014 | Golder |
| 8,801,903 B2 | 8/2014 | Mourad et al. |
| D719,742 S | 12/2014 | Seitzinger et al. |
| D721,509 S | 1/2015 | Gunter |
| D727,983 S | 4/2015 | Lee et al. |
| D728,243 S | 5/2015 | Paetzel |
| D731,644 S | 6/2015 | Robles et al. |

(56) References Cited

U.S. PATENT DOCUMENTS

| | | | |
|---|---|---|---|
| 9,090,288 B2 | 7/2015 | Takahashi | |
| D737,998 S | 9/2015 | Lee et al. | |
| D740,570 S | 10/2015 | Seitzinger et al. | |
| D762,992 S | 8/2016 | Rutter | |
| D764,184 S | 8/2016 | Paetzel | |
| 9,427,021 B2 | 8/2016 | Zitturi et al. | |
| D770,188 S | 11/2016 | Fang | |
| D774,314 S | 12/2016 | Gutierrez Diaz et al. | |
| D777,452 S | 1/2017 | Toronjo | |
| D779,655 S | 2/2017 | Brown et al. | |
| D782,797 S | 4/2017 | Cin et al. | |
| D782,798 S | 4/2017 | Cin et al. | |
| 9,771,675 B2 | 9/2017 | Altshuler et al. | |
| D804,549 S | 12/2017 | Ferronato | |
| 2001/0046826 A1 | 11/2001 | Tebbe | |
| 2002/0112829 A1 | 8/2002 | Von Paleske et al. | |
| 2003/0003826 A1* | 1/2003 | Rudisill | B32B 5/26 442/36 |
| 2003/0041953 A1* | 3/2003 | Farell | D04H 1/544 156/181 |
| 2004/0043183 A1 | 3/2004 | Thrasher et al. | |
| 2004/0118530 A1 | 6/2004 | Kressner et al. | |
| 2004/0241399 A1 | 12/2004 | Marmon et al. | |
| 2005/0204449 A1 | 9/2005 | Baron et al. | |
| 2006/0057921 A1* | 3/2006 | Turi | D04H 3/14 442/327 |
| 2006/0063456 A1 | 3/2006 | Carter | |
| 2007/0137813 A1 | 6/2007 | Nickel et al. | |
| 2007/0161304 A1 | 7/2007 | Wangbunyen | |
| 2007/0218248 A1 | 9/2007 | Mansson et al. | |
| 2007/0254145 A1 | 11/2007 | Sawin et al. | |
| 2008/0218369 A1 | 9/2008 | Krans et al. | |
| 2008/0268194 A1* | 10/2008 | Kim | D04H 3/14 428/43 |
| 2009/0041978 A1 | 2/2009 | Sogard et al. | |
| 2009/0111347 A1 | 4/2009 | Peng et al. | |
| 2009/0211620 A1 | 8/2009 | Dibachi et al. | |
| 2010/0048072 A1* | 2/2010 | Kauschke | A47L 13/16 442/1 |
| 2010/0075120 A1* | 3/2010 | Gustafsson | B32B 5/26 428/196 |
| 2010/0186913 A1 | 7/2010 | Super et al. | |
| 2010/0297335 A1 | 11/2010 | Mellin et al. | |
| 2011/0083246 A1 | 4/2011 | Vitarana | |
| 2012/0021178 A1 | 1/2012 | Miller et al. | |
| 2012/0034483 A1 | 2/2012 | Mair | |
| 2012/0315440 A1* | 12/2012 | Ichikawa | D04H 3/14 428/156 |
| 2013/0288013 A1* | 10/2013 | Jones | D04H 3/14 428/172 |
| 2013/0330486 A1 | 12/2013 | Shields | |
| 2014/0155854 A1* | 6/2014 | MacDonald | D04H 1/435 604/372 |
| 2015/0101772 A1* | 4/2015 | Olson | D21H 27/40 162/109 |
| 2017/0016158 A1* | 1/2017 | Burgess | A61F 13/00 |
| 2017/0027774 A1* | 2/2017 | Ashraf | A61F 13/55145 |
| 2017/0029993 A1* | 2/2017 | Ashraf | D04H 3/018 |
| 2017/0029994 A1* | 2/2017 | Ashraf | D04H 3/16 |
| 2017/0191198 A1* | 7/2017 | Ashraf | D04H 3/16 |
| 2017/0332873 A1 | 11/2017 | Yamada | |

FOREIGN PATENT DOCUMENTS

| | | | |
|---|---|---|---|
| EP | 2821043 A1 * | 1/2015 | A61F 13/51476 |
| EP | 2821043 A1 | 1/2015 | |
| EP | 3187635 A1 | 5/2017 | |
| EP | 3187635 A1 * | 7/2017 | D04H 1/54 |
| JP | 2005245913 A * | 9/2005 | |
| JP | 2014188042 A * | 10/2014 | |
| JP | 2015112340 A * | 6/2015 | D04H 1/54 |
| WO | 199724482 | 7/1997 | |
| WO | WO-0109425 A1 * | 2/2001 | B32B 5/26 |
| WO | 2012024576 A1 | 2/2012 | |

OTHER PUBLICATIONS

Written Opinion relating to International Application No. PCT/US2016/061891, dated Feb. 1, 2017.

Bishamon Kikko Red fabric—nekineko—Spoonflower (on-line), dated Nov. 7, 2016. Retrieved from Internet Mar. 27, 2018, URL: https://web.archive.orgtweb/201611 07180452/https:/fwww.spoonflower.com/fabric/111 0953--bishamon-kikko-red-by-nekineko (2 pages).

* cited by examiner

NONWOVEN WITH IMPROVED ABRASION RESISTANCE AND METHOD OF MAKING THE SAME

RELATED APPLICATIONS

This non-provisional application claims priority to U.S. Provisional Patent Application 62/254,496, entitled NONWOVEN WITH IMPROVED ABRASION RESISTANCE AND METHOD OF MAKING THE SAME, filed Nov. 12, 2015, the contents of which are incorporated herein by reference in their entirety.

FIELD OF THE INVENTION

The present invention relates to fusion bonded patterned nonwovens that are abrasion resistant and to methods for producing the same.

SUMMARY OF THE INVENTION

The present invention is directed to a patterned nonwoven web that has a high abrasion resistance and to a method of making the same, wherein the abrasion resistance is derived, at least in part, from the bond pattern that is used during the formation of the web. The abrasion resistant, patterned nonwoven may be used, for example, with disposable absorbent articles, such as disposable diapers, incontinence and feminine care products, and disposable products for the medical and other industries.

An exemplary bond pattern that is used to form the patterned nonwoven web includes closed figures, which may be geometric or irregular, formed from continuous bond lines where the closed figures are spaced apart. The bond pattern may be formed, for example, by thermal or ultrasonic bonding.

In at least one embodiment, one preferred bond pattern comprises a pattern of circles. More particularly, in at least one embodiment, the bond pattern comprises circles having a diameter in a range of 5-15 mm in diameter, a bond line width within a range of 0.1 mm to 1.5 mm and a distance between adjacent circles of the pattern within a range of 0.0 to 10.0 mm. Also, in at least one embodiment, the total percentage bond area of the nonwoven web is between 5 to 30%, and more preferably between 10 to 25%.

A nonwoven web according to an exemplary embodiment of the present invention comprises: a first layer comprising continuous fibers including a first polymer component, the first layer being bonded with a bond pattern including spaced apart closed figures arranged in a repeating pattern.

In at least one embodiment, the closed figures are rounded figures.

In at least one embodiment, the closed figures are circles.

In at least one embodiment, the closed figures are polygons.

In at least one embodiment, the bond pattern includes additional bond elements.

In at least one embodiment, the additional bond elements contain continuous bond lines.

In at least one embodiment, the additional bond elements are disposed within the closed figures.

In at least one embodiment, the nonwoven web includes a secondary pattern.

In at least one embodiment, the secondary pattern is embossed.

In at least one embodiment, the secondary pattern comprises mechanically, hydraulically or thermomechanically (e.g., hot needles) formed apertures or perforations.

In at least one embodiment, the secondary pattern is hydraulically patterned.

In at least one embodiment, the secondary pattern is ultrasonically bonded.

In at least one embodiment, the secondary pattern is registered with the first pattern.

In at least, one embodiment, the secondary pattern is not registered with the first pattern.

In at least one embodiment, the secondary pattern increases the HOM of the nonwoven web by less than 1 gram.

In at least one embodiment, the secondary pattern decreases the HOM of the nonwoven by at least 1 gram.

In at least one embodiment, the first polymer component is polypropylene.

In at least one embodiment, the continuous fibers of the first layer include a second polymer component.

In at least one embodiment, the second polymer component is polyethylene and/or blends of different polyethylenes and additives or polypropylene and/or blends of different polypropylenes and additives or copolymers of polypropylene and polyethylene.

In at least one embodiment, the continuous fibers of the first layer are bicomponent or multicomponent fibers.

In at least one embodiment, the first layer includes non-continuous fibers.

In at least one embodiment, the non-continuous fibers are staple fibers.

In at least one embodiment, the nonwoven web has a basis weight within the range of 5 gsm to 60 gsm.

In at least one embodiment, the nonwoven web has an Abrasion Rating of 4 or higher and an Average HOM of less than 6 grams.

In an exemplary embodiment, an absorbent article includes, in a cross sectional view from top to bottom, a topsheet, an absorbent core, and a backsheet, wherein the topsheet comprises a nonwoven web that comprises: a first layer comprising continuous fibers including a first polymer component, the first layer being bonded with a bond pattern including spaced apart closed figures arranged in a repeating pattern.

In an exemplary embodiment, an absorbent article includes, in a cross sectional view from top to bottom, a topsheet, an absorbent core, and a backsheet, wherein the backsheet comprises a nonwoven web that comprises: a first layer comprising continuous fibers including a first polymer component, the first layer being bonded with a bond pattern including spaced apart closed figures arranged in a repeating pattern.

A nonwoven web according to an exemplary embodiment of the present invention comprises: a first layer comprising non-continuous fibers including a first component, the first layer being bonded with a bond pattern including spaced apart closed figures arranged in a repeating pattern.

In at least one embodiment, the first component is polypropylene.

In at least one embodiment, the first component is at least one of synthetic or organic short fiber material.

In at least one embodiment, the first component is viscose;

In at least one embodiment, the first component is cellulose;

In at least one embodiment, the first component is cotton.

According to an exemplary embodiment of the present invention, a method of making a patterned nonwoven web comprises: forming a nonwoven web comprising: a first layer comprising continuous fibers; bonding the first layer with a bond pattern containing spaced apart closed figures arranged in a repeating pattern.

In at least one embodiment, the step of forming a nonwoven web comprises a spunmelt process.

In at least one embodiment, the bonding is thermal bonding.

In at least one embodiment, the bonding is ultrasonic bonding.

In at least one embodiment, the method further including a hydraulic treatment step.

In at least one embodiment, method further including bonding the nonwoven web to a second web.

In at least one embodiment, the second web is a film.

In at least one embodiment, the second web is a nonwoven web.

In at least one embodiment, the second web is a nonwoven web including staple fibers.

In at least one embodiment, the second web is a paper or tissue web.

Other features and advantages of the present invention will become readily apparent from the following detailed description and the accompanying drawings.

BRIEF DESCRIPTION OF THE DRAWINGS

The above and related objects, features and advantages of the present invention will be more fully understood by reference to the following, detailed description of the preferred, albeit illustrative, embodiment of the present invention when taken in conjunction with the accompanying figures, wherein.

DETAILED DESCRIPTION

The present invention is directed to a patterned nonwoven web that has high abrasion resistance combined with excellent drape and flexibility and a method of making the same. In the present invention, the abrasion resistance and drape of the nonwoven web is at least partially dependent upon the fusion bond pattern that is used to bond together continuous spunmelt filaments, carded fibers or combinations of the filaments and fibers (where multiple webs are combined together) so that the resulting nonwoven is abrasion resistant, yet still soft and flexible.

In embodiments, a bond pattern may include closed figures having geometric or irregular shapes, at least partially separated from each other by an unbonded area. For the purposes of the present disclosure, the term "closed figure" is intended to mean an area of unbonded fibers that is defined by either continuous or discontinuous bond lines. In an exemplary embodiment, the bond pattern may be made up of grid lines so that there are no spaces between the repeating figures that make up the pattern. The bond pattern may also include additional bond elements such as points or lines. The pattern preferably bonds together all, or almost all, of the filaments or fibers in the nonwoven in discrete portions or sections along the longitudinal extension of the filaments and fibers. The patterned nonwoven is preferably abrasion resistant so that the nonwoven does not significantly degrade when abraded by another material or a wearer. "Abrasion resistance" is used herein to mean "the ability of the nonwoven to resist surface wear caused by flat rubbing contact with a wearer or with another material." At the same time, the nonwoven remains soft and flexible.

The nonwoven web formed using the bond pattern in accordance with the present invention is especially suitable for use in disposable absorbent articles. As used herein, the term "absorbent article" refers to articles which absorb and contain fluids and solid materials. For example, absorbent articles may be placed against or in proximity to the body to absorb and contain the various exudates discharged by the body. Absorbent articles may be articles that are worn, such as baby diapers, adult incontinence products, and feminine care products, or hygienic products that are used to absorb fluids and solid materials, such as for the medical profession, specific examples being disposable gowns and chucks. The nonwovens may also be used for packaging or wrapping items such as absorbent articles. The term "disposable" is used herein to describe absorbent articles which are not intended to be laundered or otherwise restored or reused as an absorbent article, but instead are intended to be discarded after a single use and, preferably, to be recycled, composted or otherwise disposed of in an environmentally compatible manner.

Figure 1:
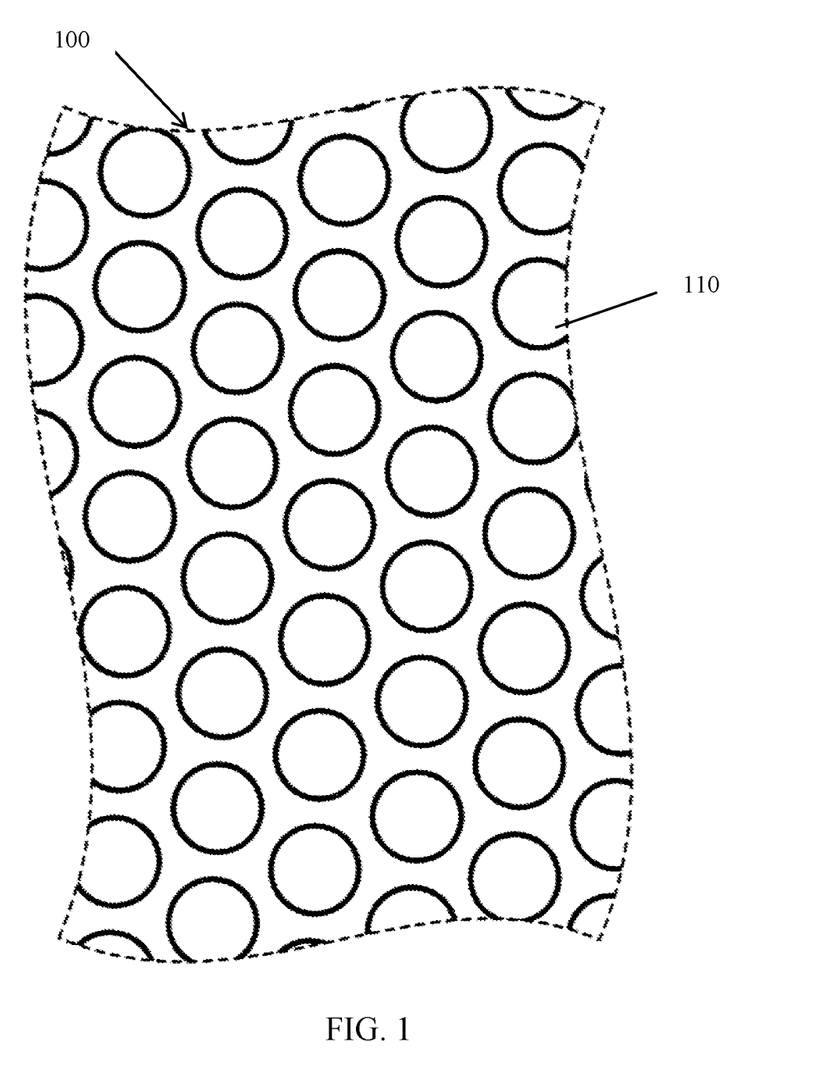
FIG. 1 is a top view of a nonwoven web having a circular bond pattern formed thereon in accordance with an exemplary embodiment of the present invention.
Figure 2:
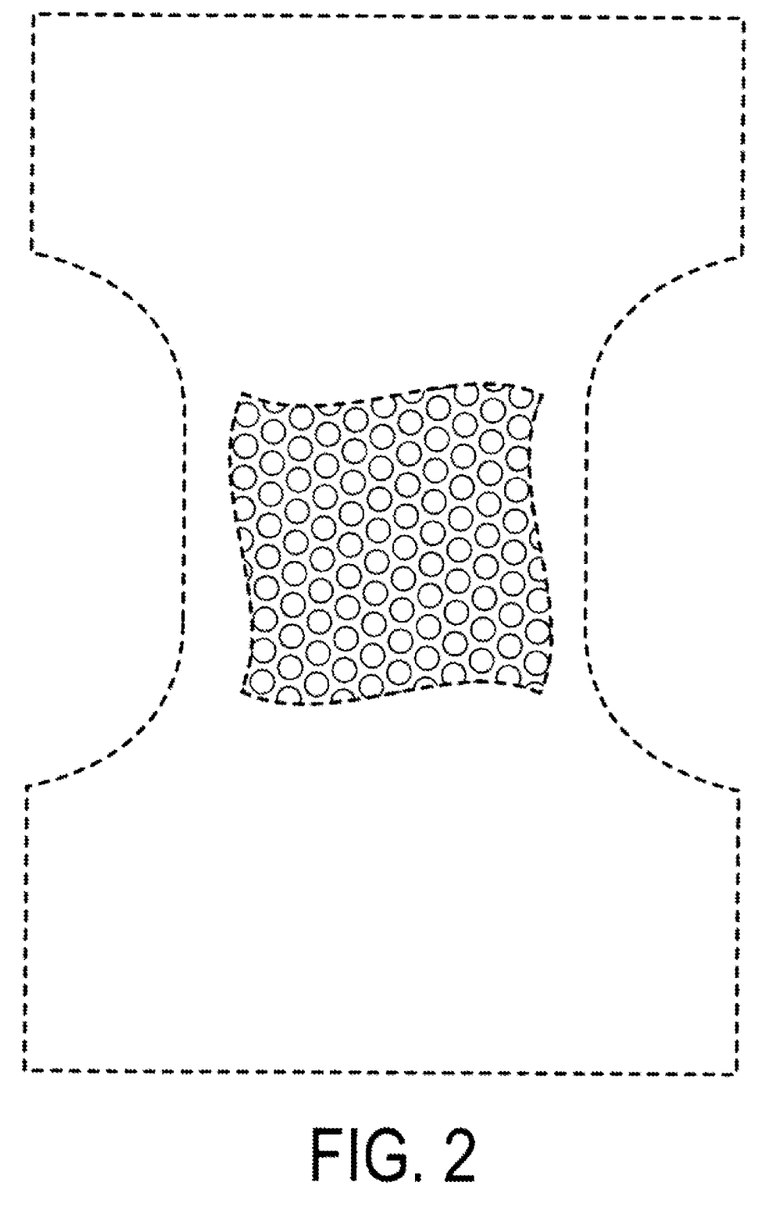
FIG. 2 is a perspective view of a nonwoven topsheet of a diaper formed with the bond pattern of FIG. 1 in accordance with an exemplary embodiment of the present invention.
Figure 3:
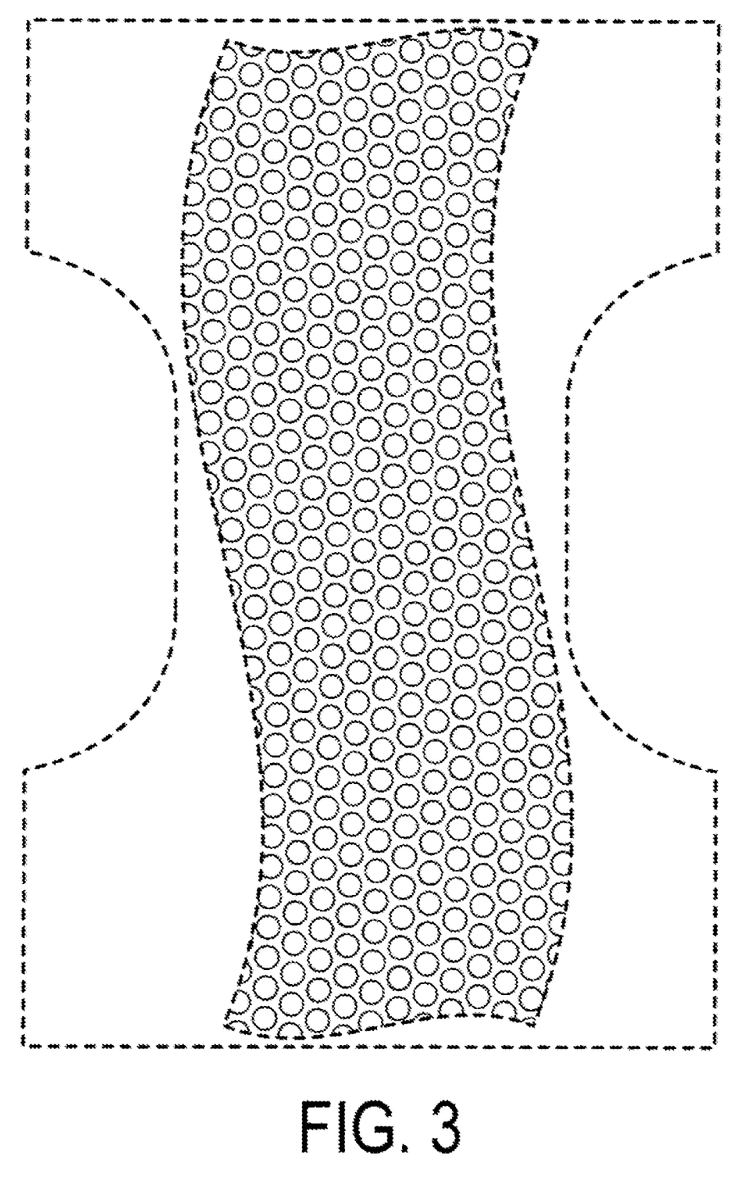
FIG. 3 is a perspective view of a nonwoven backsheet of a diaper formed with the bond pattern of FIG. 1 in accordance with an exemplary embodiment of the present invention.

FIG. 1 shows a perspective view of an exemplary embodiment of a bond pattern formed on a nonwoven web that has been determined to achieve a nonwoven having a high abrasion resistance and strength, while maintaining the softness and flexibility desired in a nonwoven. The bond pattern of FIG. 1 is shown in FIG. 2 in the context of a nonwoven web that is attached to an absorbent article, such as to the chassis of a diaper. For example, a nonwoven web may be a layer in the topsheet of a diaper as shown in FIG. 2. Alternatively, for example, the nonwoven web may be the outer layer of a film/nonwoven composite backsheet of the diaper, as shown in FIG. 3.

It has been found desirable to form bond patterns from continuous bond lines arranged in closed figures as this results in nonwoven webs having improved abrasion resistance while retaining flexibility. Without being bound by theory, it is believed that placing the closed figures in staggered positions minimizes unbonded loose fibers or filament ends, thus improving abrasion resistance. A preferred embodiment of such closed figures is circles or other rounded figures, but other figures such as polygons or combinations of shapes may also be used.

Closed figures may also be used in combination with other types of bonds such as point bonds or bond lines. These additional elements may be disposed within the closed figures. Further, additional bonds may be used for decorative or aesthetic purposes. In this regard, additional bonds may be formed through a different bonding method than the bonding method used for the closed figures. These elements are designed to not significantly influence the softness and drape of the nonwoven. In another alternative, embossments may be used instead of the additional bonds. In at least one embodiment, a secondary pattern, such as a pattern of apertures, may be applied that provides functional, decorative and/or aesthetic benefits without substantially reducing the drape of the nonwoven. The secondary pattern may be registered with the pattern of closed figures. Alternatively, the secondary pattern may be applied without being registered to the pattern of closed figures.

Figure 4:
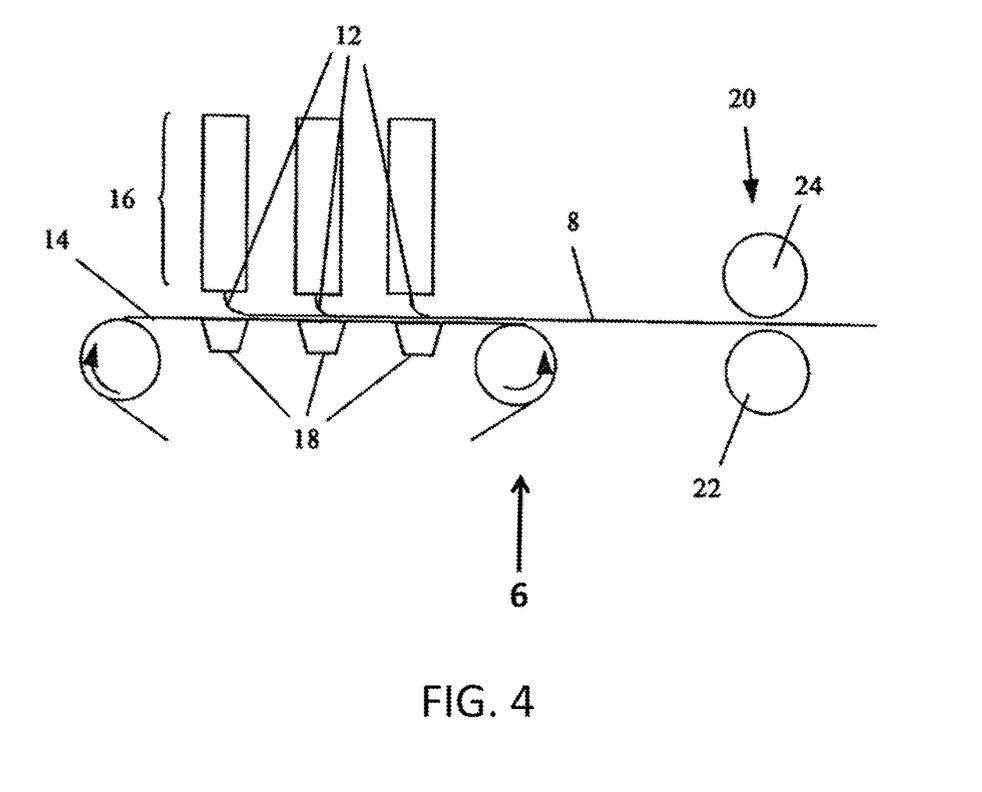
FIG. 4 is a representative diagram of a system for forming a patterned nonwoven web according to an exemplary embodiment of the present invention.

FIG. 4 is a representative diagram of a system, generally designated by reference numeral 6, for forming a patterned nonwoven web according to an exemplary embodiment of the present invention in which a spunbond, meltblown or spunbond-meltblown-spunbond composite ("SMS") nonwoven is formed. The method begins with a nonwoven web of continuous fibers formed by processes well known in the art. In the illustrated exemplary embodiment, the web is preferably "meltspun"—that is, the nonwoven web is meltblown, spunbond or a combination thereof. In a preferred embodiment, the fibers used to form the web are thermoplastic or spinnable polymers, examples of which include polyolefins, polyesters, polyamides, copolymers thereof (with olefins, esters, amides or other monomers) and blends thereof. As used herein, the term "blend" includes either a homogeneous mixture of at least two polymers or a non-homogeneous mixture of at least two physically distinct polymers as used for bicomponent fibers or filaments preferably arranged or combined as sheath-core or side-by-side configurations. Preferably the fibers are polyolefins, examples of which include polyethylene, polypropylene, propylene-butylene copolymers thereof and blends thereof, including, for example, ethylene/propylene copolymers and polyethylene/polypropylene blends. In an even more preferred embodiment, the fibers are bicomponent or multicomponent fibers. According to an exemplary embodiment, the fibers are polypropylene fibers having a linear mass density within a range of 1.1 to 5.0 denier, and in a preferred embodiment the linear mass density is within a range of 1.1 to 2.5 denier, and in another preferred embodiment the liner mass density is within a range of 1.1 to 1.8 denier. Fibers having linear mass densities greater than or less than 1.8 denier may alternatively be used.

As shown in FIG. 4, a spunmelt nonwoven web 10 according to an exemplary embodiment of the invention is made of continuous filaments 12 that are laid down on a moving conveyor belt 14 in a randomized distribution. In a typical spunmelt process, resin pellets are processed under heat into a melt and then fed through a spinneret to create hundreds of filaments 12 by use of a drawing device 16. Multiple spinnerets or beams may be used to provide an increased density of spunbond fibers. Although FIG. 4 shows the use of three beams, any number of beams may be used, such as, for example, two or four beams. Jets of a fluid (such as air) cause the fibers 12 to be elongated, and the fibers 12 are then blown or carried onto a moving foraminous belt 14 where they are laid down and sucked against the foraminous belt 14 by suction boxes 18 in a random pattern to create a fabric structure 8.

The typical thermal bonding station 20 includes a calender 22 having a bonding roll 24 defining a bond pattern. Alternatively, the thermal bonding station 20 may have an ultrasonic device or a through-air bonding device using air at elevated temperatures sufficient to cause thermal bonding between the filaments and/or fibers at their intersecting portions by melting the lower melt temperature polymeric component.

Figure 7A:
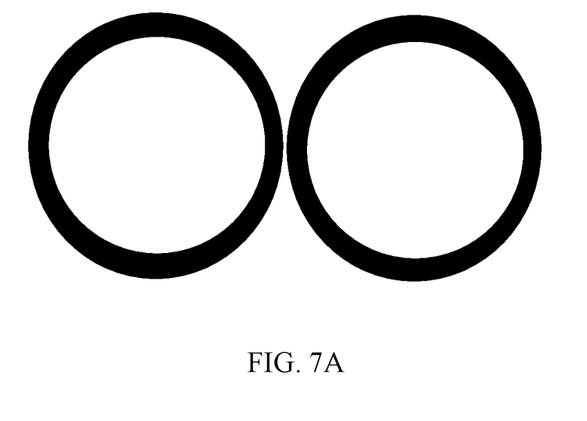
FIGS. 7A, 7B, and 7C show various circle arrangements within a bond pattern according to an exemplary embodiment of the present invention.
Figure 7B:
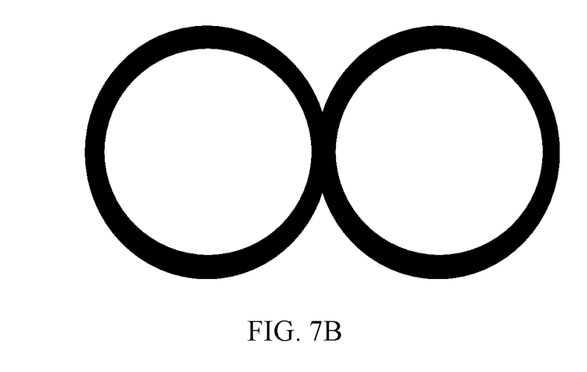
Figure 7C:
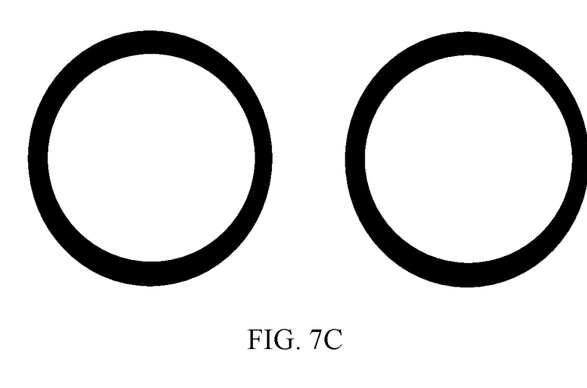
Figure 8:
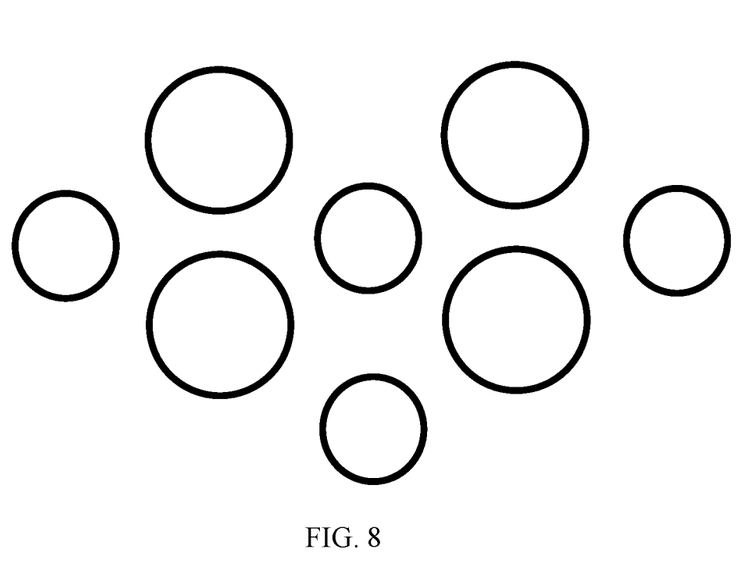
FIG. 8 shows circle arrangements within a bond pattern according to an exemplary embodiment of the present invention.

Bond patterns from bond lines arranged in closed figures may be used during thermal bonding at station 20 as this will result in the formation of a nonwoven web having an improved abrasion resistance while retaining flexibility. For example, the exemplary pattern of circles shown in FIG. 1 may be formed in accordance with the present invention during thermal bonding, such as at station 20. In a preferred embodiment, the bond pattern 100 of FIG. 1 comprises circles 110 having a diameter in a range of 5-15 mm, and more preferably 10 mm in diameter. If short (i.e., discontinuous) fibers are used to form the nonwoven, the fiber length is preferably twice the maximum diameter of the closed figures that make up the pattern. In this embodiment, the circles have a bond line width within a range of 0.3 mm to 1.5 mm and more preferably 0.4 mm to 0.8 mm. As shown in FIGS. 7A-7C, adjacent circles within the pattern may be arranged so that the adjacent circles contact one another along a common tangent line (FIG. 7A), the adjacent circles overlap (FIG. 7B) and/or the adjacent circles are spaced from one another by some distance (FIG. 7C). Further, as shown in FIG. 8, the circles may be arranged in staggered columns, with circles within one column having a different diameter as compared to circles within an adjacent column. Without being bound by theory, it is believed that such an arrangement bonds all or almost all of the filaments or fibers in the nonwoven and effectively ties down the free ends of the fibers, thus providing abrasion resistance. In an exemplary embodiment using a spunbond nonwoven, the minimum distance between the adjacent staggered circles may be within a range of between 2.0 to 3.5 mm, and is more preferably a minimum of 3 mm. Also, the total percentage of the bond area, which is the ratio of bond line width to non-bonded area, is between 5 to 30%, more preferably between 10 to 25%, and even more preferably about 14%. The depth of the convex engraving on the bond roll surface is in the range from 0.2 mm to 1.2 mm and is more preferably 1 mm.

Figure 9A:
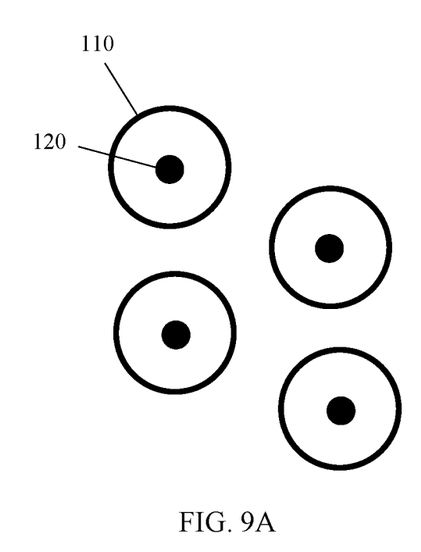
FIGS. 9A and 9B show a bond pattern formed within a nonwoven along with a secondary pattern according to an exemplary embodiment of the present invention.
Figure 9B:
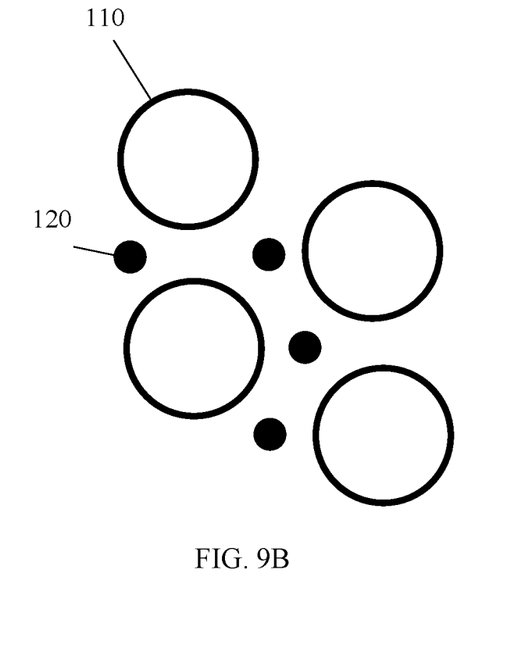

As shown in FIGS. 9A and 9B, the circles 110 (or other closed bond line shapes) may be arranged relative to a secondary pattern of apertures 120. The apertures 120 may be registered with the circles 110 (FIG. 9A) or not registered with the circles 110 (FIG. 9B). The apertures 120 may be formed hydraulically, mechanically or by any other process.

After thermal bonding, in the exemplary embodiment, the nonwoven web 10 may be hydraulically treated, such as via hydroentanglement or hydroengorgement. In a preferred embodiment, the nonwoven web 10 is subjected to hydroengorgement. The hydraulic treatment may be performed in a single step or in two or more separate steps. If the nonwoven web 10 is hydraulically treated, the nonwoven web 10 is subsequently subjected to dewatering. Dewatering may include suction boxes that draw water out of the nonwoven web 10 as the nonwoven web 10 progresses over a dewatering wire. The nonwoven web 10 is then brought to a drying station for drying before the finished material is reeled up at winding station and converted. Drying can be performed by blowing hot air through the fibrous web, by IR dryers or other drying technique.

Before conversion, the nonwoven web 10 may be subjected to treatments, such as corona or plasma treatment, treatment with topical chemicals of any desired kind, etc. Corona or plasma treatment is preferably performed on a dry web while topical chemicals may be added preferably in an aqueous solution after dewatering of the web by spraying, printing or the like.

The nonwoven web 10 may be incorporated into a nonwoven laminate. The nonwoven laminate may include additional layers of continuous fibers such as spunbond fibers and meltblown fibers and may include composite nonwovens such as spunbond-meltblown-spunbond laminates. The nonwoven laminate may also include short fibers such as staple fibers or may include pulp fibers. These short fibers may be in the form of a consolidated web such as carded web or tissue sheet or may be initially unconsolidated. The nonwoven laminate may also include superabsorbent material, either in particulate form or in a fiberized form. The laminate may be formed through conventional means, including but not limited to thermal bonding, ultrasonic bonding, chemical bonding, adhesive bonding and/or hydroentanglement.

The nonwoven web 10 may be incorporated with a cotton fiber layer for form a composite web, with the cotton fibers making up 5% to 30% of the composite web.

In an exemplary embodiment, if the area within the circle that makes up the bond pattern is 20 mm$^2$ or less, the ratio between the area within the circle and the width of the bond line that forms the circle is within the range of 20 to 200. If the area within the circle is from 20 mm$^2$ to 100 mm$^2$, the ratio between the area within the circle and the width of the bond line that forms the circle is in the range from 50 to 400. If the area within the circle is from 100 mm$^2$ to 1000 mm$^2$, the ratio between the area within the circle and the width of the bond line that forms the circle is in the range from 100 to 1000.

In an exemplary embodiment, if the diameter or maximum possible length of a filament/fiber across the encircled area is 5 mm or less, the ratio between the diameter or maximum possible length of a filament/fiber and the width of the bond line is within the range of 10 to 50. If the diameter or maximum possible length of a filament/fiber across the encircled area is 5 mm to 10 mm, the ratio between the diameter or maximum possible length of a filament/fiber and the width of the bond line is within the range of 10 to 100. If the diameter or maximum possible length of a filament/fiber across the encircled area is 10 mm to 15 mm, the ratio between the diameter or maximum possible length of a filament/fiber and the width of the bond line is within the range of 10 to 150.

In exemplary embodiments in which the bond lines that form the circle are discontinuous, the line interruption or gap, inline with the bond line's general direction, is in the range of 0.1 mm to 3.0 mm, more preferably within the range of 0.1 mm to 1.0 mm. The ratio between the uninterrupted portion of the bond line and the linear gap extension is preferably within the range of 5 to 50.

The following test methods were used to obtain data provided herein.

Abrasion Test

NuMartindale Abrasion is a measure of the abrasion resistance of the surface of a fabric sample and is performed in accordance with ASTM D 4966-98, which is hereby incorporated by reference. The NuMartindale Abrasion test was performed on each sample with a Martindale Abrasion and Pilling Tester by performing 40 to 80 abrasion cycles for each sample. Testing results were reported after all abrasion cycles were completed or destruction of the test sample. Preferably, there should be no visual change to the surface of the material.

For each sample, following NuMartindale Abrasion, an abrasion rating was determined based on a visual rating scale of 1 to 5, with the scale defined as follows:

5=excellent=very low to zero fibers removed from the structure.
4=very good=low levels of fibers that may be in the form of pills or small strings.
3=fair=medium levels of fibers and large strings or multiple strings.
2=poor=high levels of loose strings that could be removed easily.
1=very poor=significant structure failure, a hole, large loose strings easily removed.

Softness Testing

Softness testing was performed with a Handle-O-Meter, manufactured by Thwing Albert of West Berlin, N.J. using test Method INDA IST 90.3-01 with a 100 mm×100 mm sample size and the results were not doubled. This device measures the flexibility and surface friction of sheeted materials such as the nonwoven webs. Testing is performed on each sample in both the machine direction and the cross direction. In performing the test, a 6.4 mm wide slot opening may be used. The peak load is captured and recorded in grams.

Image Analysis of Bond Impressions

Area and distance measurements are performed on images generated using a flat bed scanner capable of scanning at a resolution of at least 4800 dpi in reflectance mode (a suitable scanner is the Epson Perfection V750 Pro, Epson, USA). Analyses are performed using ImageJ software (Vs. 1.43u, National Institutes of Health, USA) and calibrated against a ruler certified by NIST.

To obtain a specimen of a nonwoven used with an absorbent article, lay the sample of an absorbent article flat on a bench, body facing surface downward, and measure the total longitudinal length of the article. Note a site 33% of the total length from the front edge of the absorbent article along the longitudinal axis and a second site, 33% of the total length from the back edge of the absorbent article. Carefully remove the nonwoven from the absorbent article. A cryogenic spray, such as Cyto-Freeze (obtained from Control Company, Houston, Tex.), may be used to separate the nonwoven from the underlying layer.

For each specimen, cut a piece 80 mm by 80 mm. For a nonwoven removed from an absorbent article, cut an 80 mm by 80 mm specimen centered at each of the sites identified above. Precondition the specimen at about 23° C.±2 C.° and about 50%±2% relative humidity for 2 hours prior to testing.

Place the specimen on the flat bed scanner, the side being analyzed facing down, with the ruler directly adjacent. Placement is such that the dimension corresponding to the MD of the nonwoven is parallel to the ruler. A black backing is placed over the specimen and the lid to the scanner is closed. Acquire an image composed of the nonwoven and ruler at 4800 dpi in reflectance mode in 8 bit grayscale and save the file. Open the image file and perform a linear calibration using the imaged ruler. These measures are equally applicable to other bond shapes and repeating bond patterns.

Bond Area Percentage

The "Bond Area Percentage" on a nonwoven web is a ratio of area occupied by bond impressions, to the total surface area of the web, expressed as a percentage, and measured according to the Bond Area Percentage method set forth herein. The method for measuring Bond Area Percentage is described in U.S. Pat. No. 8,841,507, herein incorporated by reference.

The following example and comparative examples illustrates the advantages of the present invention.

EXAMPLE 1

Example 1 is a 21.3 gsm spunbond nonwoven web made from polypropylene that was thermally bonded with the bond pattern shown in FIG. 1, having a bond area percentage of approximately 14%.

COMPARATIVE EXAMPLE NO. 1

Figure 5:
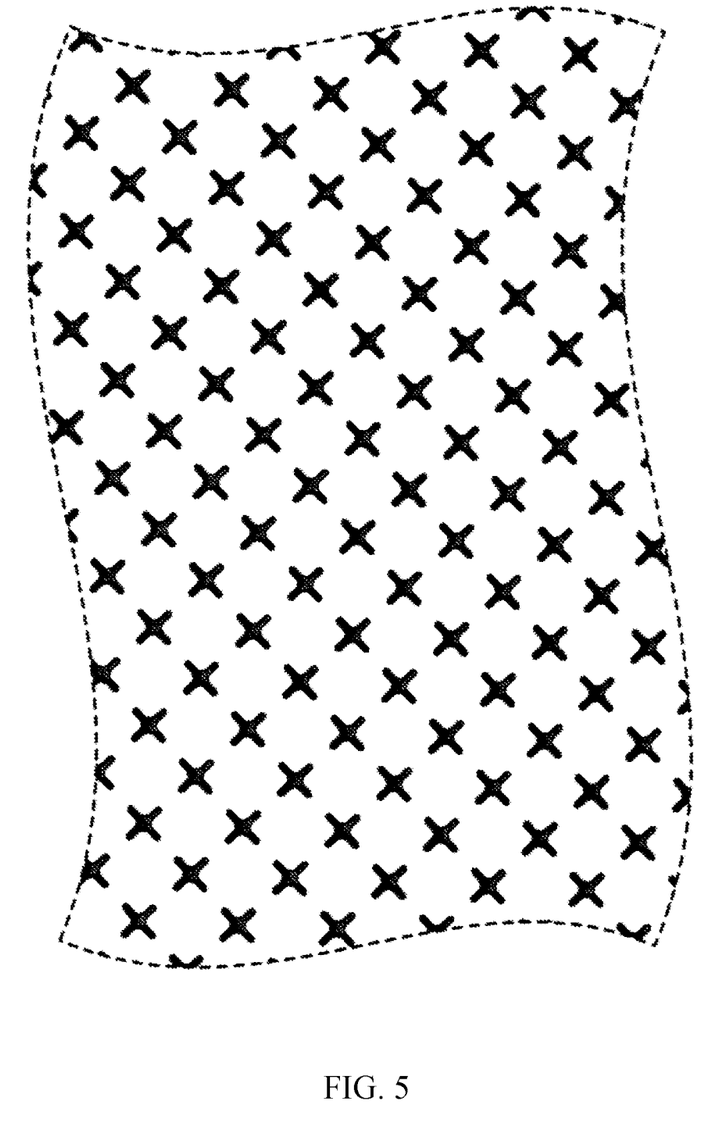
FIG. 5 is a top view of a comparative bond pattern.

Comparative Example 1 is a 20.2 gsm spunbond nonwoven web made from polypropylene and thermally bonded with the open bond pattern shown in FIG. 5 having a bond area percentage of approximately 14%.

COMPARATIVE EXAMPLE NO. 2

Figure 6:
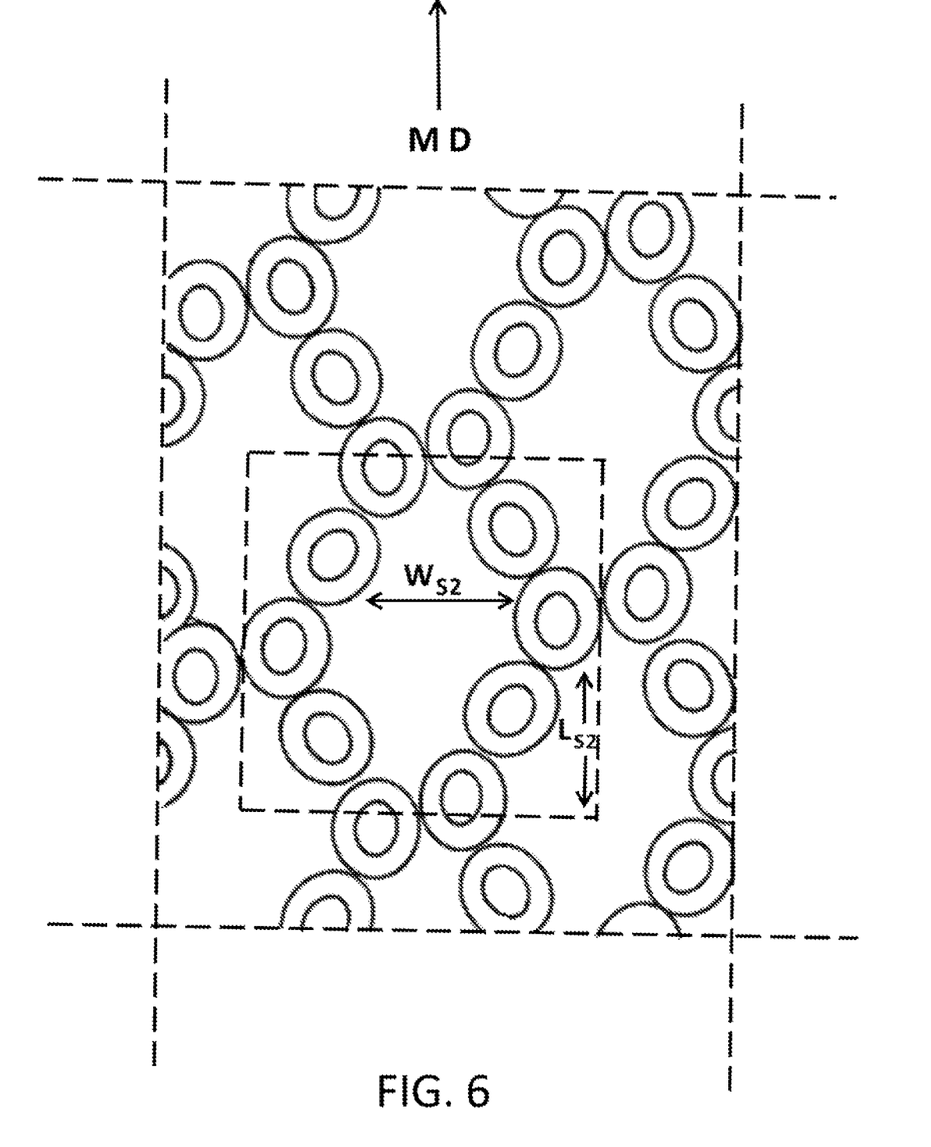
FIG. 6 is a top view of a commercially available bond pattern.

Comparative Example 2 is a 21.8 gsm spunbond nonwoven web made from polypropylene and thermally bonded with the closed bond pattern shown in FIG. 6, having a bond area percentage of approximately 18%.

TABLE I shows a comparison between the results of tests performed on Example 1, Comparative Example No. 1, and Comparative Example No. 2. As noted, Example 1 was found to have excellent abrasion resistance, while Comparative Example 1, with a similar percent bond area, did not. While Comparative Example 2 also had good abrasion resistance properties, it was significantly less drapeable than Example 1.

The results show that the pattern of Example 1 provides excellent abrasion resistance and drapeability. Thus, it is advantageous to use a closed bond pattern for bonding together the fibers of a spunbond nonwoven.

TABLE I

|  | Example 1 (FIG. 1) | Comparative Example No. 1 (FIG. 5) | Comparative Example No. 2 (FIG. 6) |
| --- | --- | --- | --- |
| Bond Area, % | 14% | 14% | 18% |
| Open Area, mm$^2$ | 100 | 55 | 5 |
| Basis Weight, gsm | 21.3 | 20.2 | 21.8 |
| Thickness, mm | 0.403 | 0.413 | 0.198 |
| Density, g/cc | 0.053 | 0.049 | 0.110 |
| Air Perm, cfm | 894 | 835 | 640 |
| MDT, N/cm | 6.0 | 5.8 | 9.1 |
| MDE, % | 66.9 | 88.6 | 75.7 |
| CDT, N/cm | 3.3 | 3.2 | 6.1 |
| CDE, % | 84.1 | 83.3 | 80.6 |
| MD HOM, g | 6.6 | 5.6 | 10.2 |
| CD HOM, g | 4.7 | 4.1 | 5.0 |
| Average HOM, g | 5.7 | 4.8 | 7.6 |
| Abrasion Rating | 5 (Excellent) | 2 (Poor) | 5 (Excellent) |

Now that embodiments of the present invention have been shown and described in detail, various modifications and improvements thereon will become readily apparent to those skilled in the art. Accordingly, the spirit and scope of the present invention is to be construed broadly and not limited by the foregoing specification.

The invention claimed is:

1. A nonwoven web made up of continuous fibers that include a polymer component, the web being bonded by a bond pattern including spaced apart closed figures arranged in a repeating pattern and unbonded spaces between the spaced apart closed figures, wherein the closed figures each having a continuous bond line surrounding a respective area that is non-bonded, and the web having a Martindale abrasion rating of 3 or higher and an average Handle-O-Meter (HOM) of less than 6 grams-force, wherein the average HOM is an average of a Machine Direction (MD) HOM value and a Cross Direction HOM value, and the nonwoven web does not include point bonds.

2. The nonwoven web of claim 1, wherein the closed figures are rounded figures.

3. The nonwoven web of claim 1, wherein the closed figures are circles.

4. The nonwoven of claim 3, wherein, if the area within each circle that makes up the bond pattern is 20 mm$^2$ or less, a ratio between the area within the circle and a width of a bond line that forms the circle is within the range of 20 to 200.

5. A nonwoven web made up of continuous fibers that include a polymer component, the web being bonded by a bond pattern including spaced apart closed figures arranged in a repeating pattern and unbonded spaces between the spaced apart closed figures, wherein the closed figures are circles and the closed figures each having a continuous bond line surrounding a respective area that is non-bonded, and the web having a Martindale abrasion rating of 3 or higher, wherein, if the area within each circle that makes up the bond pattern is from 20 mm$^2$ to 500 mm$^2$, a ratio between an area within the circle and a width of the bond line that forms the circle is in the range of 20 mm to 500 mm, and the nonwoven web does not include point bonds.

6. The nonwoven of claim 3, wherein, if the area within the circle that makes up the bond pattern is from 100 mm$^2$ to 1000 mm$^2$, a ratio between the area within the circle and a width of a bond line that forms the circle is in the range of 100 to 1000.

7. The nonwoven of claim 3, wherein, if a diameter of each circle that makes up the bond pattern or a maximum possible length of a filament or fiber across the encircled area is 5 mm or less, a ratio between the diameter or the maximum possible length of a filament or fiber and a width of a bond line that forms the circle is within the range of 10 to 50.

8. The nonwoven web of claim 3, wherein, if a diameter of each circle that makes up the bond pattern or a maximum possible length of a filament or fiber across the encircled area is 5 mm to 10 mm, a ratio between the diameter or the maximum possible length of a filament or fiber and a width of a bond line that forms the circle is within the range of 10 to 100.

9. The nonwoven of claim 3, wherein, if a diameter of each circle that makes up the bond pattern or a maximum possible length of a filament or fiber across the encircled area is 10 mm to 15 mm, a ratio between the diameter or the maximum possible length of a filament or fiber and a width of a bond line that forms the circle is within the range of 10 to 150.

10. The nonwoven web of claim 1, wherein the closed figures are polygons.

11. The nonwoven web of claim 1, wherein the bond pattern comprises additional bond elements.

12. The nonwoven web of claim 11, wherein the additional bond elements contain continuous bond lines.

13. The nonwoven web of claim 12, wherein the additional bond elements are disposed within the closed figures.

14. The nonwoven web of claim 1, wherein the nonwoven web comprises a secondary pattern.

15. The nonwoven web of claim 14, wherein the secondary pattern is embossed.

16. The nonwoven web of claim 15, wherein the secondary pattern is hydraulically embossed.

17. The nonwoven web of claim 15, wherein the secondary pattern is ultrasonically bonded.

18. The nonwoven web of claim 15, wherein the secondary pattern is registered with the bond pattern.

19. The nonwoven web of claim 15, wherein the secondary pattern is not registered with the bond pattern.

20. The nonwoven web of claim 14, wherein the secondary pattern is made up of apertures.

21. The nonwoven web of claim 20, wherein the apertures are formed hydraulically.

22. The nonwoven web of claim 20, wherein the apertures are formed mechanically.

23. The nonwoven web of claim 20, wherein the apertures are registered with the bond pattern.

24. The nonwoven web of claim 20, wherein the apertures are not registered with the bond pattern.

25. The nonwoven web of claim 14, wherein the secondary pattern increases the HOM of the nonwoven web by less than 1 gram.

26. The nonwoven web of claim 14, wherein the secondary pattern decreases the HOM of the nonwoven web by at least 1 gram.

27. The nonwoven web of claim 1, wherein the polymer component is polypropylene.

28. The nonwoven web of claim 27, wherein the continuous fibers comprise an additional polymer component.

29. The nonwoven web of claim 28, wherein the additional polymer component is polyethylene.

30. The nonwoven web of claim 1, wherein the continuous fibers are bicomponent or multicomponent fibers.

31. The nonwoven web of claim 1, wherein the web further comprises discontinuous fibers.

32. The nonwoven web of claim 31, wherein the discontinuous fibers are staple fibers.

33. The nonwoven web of claim 1, wherein the web has a basis weight within the range of 5 gsm to 60 gsm.

34. The nonwoven web of claim 1, wherein the nonwoven web has an abrasion rating of 4 or higher.

35. The nonwoven web of claim 1, wherein the nonwoven web has an abrasion rating of 5.

36. A nonwoven laminate comprising the nonwoven web of claim 1.

37. The nonwoven laminate of claim 1, further comprising one or more layers of continuous fibers.

38. The nonwoven laminate of claim 37, wherein the one or more layers comprise at least one of spunbond fibers or meltblown fibers.

39. The nonwoven laminate of claim 37, wherein the one or more layers comprise a spunbond-meltblown-spunbond laminate.

40. The nonwoven laminate of claim 1, further comprising one or more layers of staple fibers.

41. The nonwoven laminate of claim 1, further comprising one or more layers of pulp fibers.

42. The nonwoven laminate of claim 1, wherein the laminate is formed by at least one of thermal bonding, ultrasonic bonding, chemical bonding, adhesive bonding or hydroentanglement.

43. An absorbent article comprising the nonwoven web of claim 1.

44. The nonwoven web of claim 1, wherein the average Handle-O-Meter (HOM) of the web is at least 3 grams-force.

45. The nonwoven web of claim 1, wherein the average Handle-O-Meter (HOM) of the web is at least 4 grams-force.

46. The nonwoven web of claim 1, wherein the average Handle-O-Meter (HOM) of the web is at least 5 grams-force.

* * * * *